United States Patent [19]

Effland et al.

[11] 4,452,803
[45] Jun. 5, 1984

[54] PYRROLYLAMINOPIPERIDINES

[75] Inventors: Richard C. Effland; Joseph T. Klein, both of Bridgewater, N.J.

[73] Assignee: Hoechst-Roussel Pharmaceuticals, Inc., Somerville, N.J.

[21] Appl. No.: 533,677

[22] Filed: Sep. 19, 1983

[51] Int. Cl.³ .................. A61K 37/445; C07D 403/12; C07D 403/04
[52] U.S. Cl. .................................... 424/267; 546/208
[58] Field of Search ........................ 424/267; 546/208

[56] References Cited

U.S. PATENT DOCUMENTS 4,348,524 9/1982 Karrer et al. .................... 546/208

FOREIGN PATENT DOCUMENTS

2429923          Fed. Rep. of Germany.

OTHER PUBLICATIONS

Flitsch et al., "Chem. Ber." Vol. 102, pages 3268-3276 (1969).

Scheibye et al., "Bull. 500, Chim. Belg." Vol. 87, No. (3), pages 229-238.

Epton, "Chemistry and Industry", pages 425-426 (March 6, 1965).

Johnson et al., "J. Med. Chem.", Vol. 24, pages 1314-1319 (1961).

Neimegeers et al., "Arzneim-Forsch.) (Drug. Res.) Vol. 26, No. 8, pages 1551-1556 (1976).

Janssen et al., "Arzneim-Forsch.) Vol. 13, pages 502-507 (1963).

Primary Examiner—Robert T. Bond
Attorney, Agent, or Firm—Jerome Rosenstock

[57] ABSTRACT

This invention relates to pyrrolylaminopiperidines and related compounds of the formula

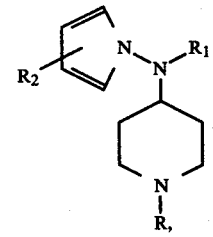

where R is hydrogen, loweralkyl, Arloweralkyl, cycloalkylloweralkyl, loweralkenyl and thienylloweralkyl; $R_1$ is lower alkyl, hydrogen, loweralkylcarbonyl, loweralkoxycarbonyl, loweralkylthiocarbonyl of the formula

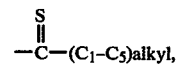

cyano, loweralkylaminocarbonyl, diloweralkylaminocarbonyl, cycloalkylcarbonyl, cycloalkylloweralkylcarbonyl and loweralkenylcarbonyl; $R_2$ is hydrogen, halogen and methyl; and the pharmaceutically acceptable acid addition salts thereof.

85 Claims, No Drawings

PYRROLYLAMINOPIPERIDINES

To the best of our knowledge the compounds of the present invention have not heretofore been described or suggested.

The compounds of the present invention have the general formula

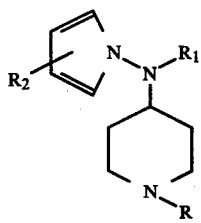
(I)

where R is hydrogen, loweralkyl, Arloweralkyl, cycloalkylloweralkyl, loweralkanoyl and thienylloweralkyl; $R_1$ is hydrogen, loweralkyl, loweralkylcarbonyl, loweralkoxycarbonyl, loweralkylthiocarbonyl

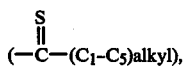

cyano, loweralkylaminocarbonyl, diloweralkylaminocarbonyl, cycloalkylcarbonyl, cycloalkylloweralkylcarbonyl and loweralkenylcarbonyl; $R_2$ is hydrogen, halogen and —$CH_3$; and the pharmaceutically acceptable salts thereof.

Particularly preferred compounds of the invention are those of Compound I where R is phenylethyl; $R_1$ is loweralkoxycarbonyl, loweralkylcarbonyl and cyano; and $R_2$ is hydrogen.

In the above definitions and as used hereinafter, the term "lower" means the group it is describing contains 1 to 6 carbon atoms. The term "alkyl" refers to a straight or branched chain hydrocarbon containing no unsaturation, e.g. methyl, ethyl, propyl, tertiary-butyl, isopropyl, etc. The term "Arloweralkyl" refers to a monovalent substitutent which consists of an aryl group, e.g. phenyl, p-nitrophenyl, o-toluyl, m-methoxyphenyl, etc., linked through a lower alkylene group having its free valence bond from a carbon of the lower alkylene group and having a formula of

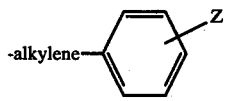

where Z is hydrogen, halogen, $CF_3$, $NO_2$, $NH_2$, loweralkyl, and loweralkoxy. The term "alkylene" refers to a bivalent radical of the lower branched or unbranched alkyl group it is derived from having valence bonds from two terminal carbons thereof, e.g., ethylene (—$CH_2CH_2$—), propylene (—$CH_2CH_2CH_2$—), isopropylene

etc. The term "alkoxy" refers to a monovalent substituent which consists of an alkyl group linked through an ether oxygen having its free valence bond from the ether oxygen, e.g. methoxy, ethoxy, isopropoxy, butoxy, etc. The term "halogen" refers to a member of the family consisting of fluorine, chlorine, bromine and iodine. The term "cycloalkylloweralkyl" refers to a monovalent substituent consisting of a saturated hydrocarbon group possessing at least one carbocyclic ring of 3 to 7 carbon atoms, e.g. cyclopropyl, cyclobutyl, cyclopentyl, cyclohexyl, cycloheptyl, etc., linked through a lower alkyl group. The term "alkenyl" refers to a straight or branched chain hydrocarbon containing one unsaturated or double bond, e.g.

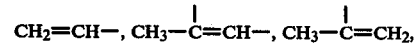

etc. The term "thienylloweralkyl" means

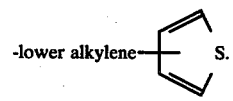

The compounds of the present invention are prepared in the following manner. The substituents R, $R_1$ and $R_2$ are as defined above unless indicated otherwise.

A substituted 1-aminopyrrole of the formula

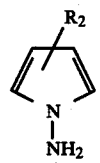
(II)

is selected. Compound II is typically prepared in the manner described in Flitsch et al., Chem. Ber. 102, 3268-3276 (1969) which describes the preparation of 1-aminopyrrole and substituted 1-aminopyrroles.

Compound II is condensed with Compound III having the formula

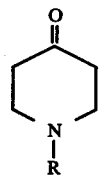
(III)

by heating at 80° to 120° C. for 2 to 24 hours in the presence of an inert solvent, e.g. benzene, toluene, cyclohexane, etc., followed by reduction with an agent such as sodium borohydride in a solvent such as isopropanol at 60°-80° to form a condensation product of the invention having the formula

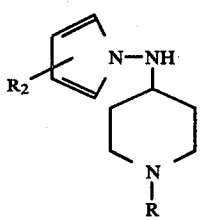

(IV)

Compound IV is reacted under conventional substitution reaction conditions, typically in the presence of a polar solvent, e.g. dimethylformamide, dichloromethane, chloroform, etc. a base, such as for example $K_2CO_3$, $Na_2CO_3$, $NaHCO_3$, etc., at a temperature of 25° to 60° C. for 2 to 24 hours, with an acid halide having the formula

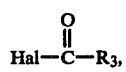

where Hal is a halogen and $R_3$ is lower alkyl of 1 to 5 carbon atoms [($C_1$-$C_5$)-alkyl], cycloalkyl and loweralkenyl of 1 to 5 carbon atoms [($C_1$-$C_5$)-alkenyl] to form a compound of the invention having a formula

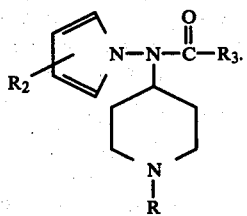

(V)

The carbonyl group of compound V in turn can be reduced in a conventional manner, e.g. with borane-tetrahydrofuran complex at a temperature of −30° C. to 0° C. for a time of 1 minute to 60 minutes, with zinc amalgam in hydrochloric acid, hydrogen in the presence of a catalyst, such as Pd, etc., to provide Compound I, where $R_1$ is loweralkyl of 1 to 6 carbon atoms, when $R_3$ is ($C_1$-$C_5$) alkyl or ($C_1$-$C_5$) alkenyl; or to provide Compound I where $R_1$ is loweralkylcycloalkyl when $R_3$ is cycloalkyl. Compound V, where $R_3$ is ($C_1$-$C_5$) alkyl, is reacted in the manner reported in *Bull. Soc. Chim. Belg.* 87, (3), 229–238 (1978) with p-methoxyphenylthionophosphine sulfide dimer to form a compound of the invention having the formula

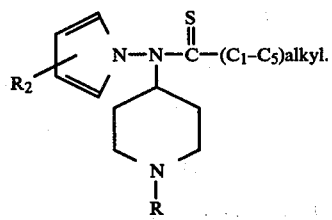

(VI)

Compound IV is reacted under conventional substitution reaction conditions with a halocyanide of the formula Hal—CN, where Hal is a halogen, e.g. Br, to form a compound of the invention having the formula

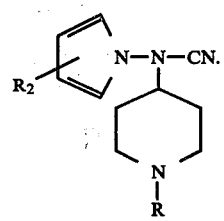

(VII)

Typically the reaction is carried out in a polar solvent, e.g. dimethylformamide, chloroform, dichloromethane, etc. at a temperature of 25° to 60° C. for 2 to 24 hours.

Compound IV is reacted, under conventional substitution reaction conditions, in a polar solvent at 25° to 60° C. for 2 to 24 hours with a haloformate ester of the formula

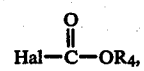

(VIII)

where Hal is a halogen and $R_4$ is a ($C_1$-$C_6$) alkyl to form a compound of the invention having the formula

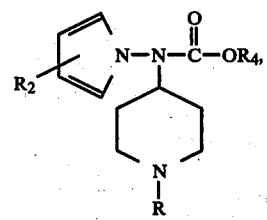

(IX)

Compound IV is reacted with an isocyanate compound of the formula $R_5$—N=C=O (X) where $R_5$ is ($C_1$-$C_6$) alkyl to form a compound of the invention having the formula

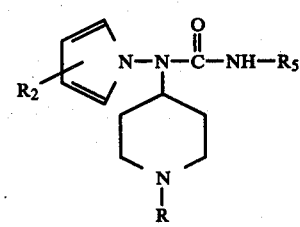

(XI)

Typically this reaction is carried out in a nonpolar solvent, e.g. benzene, toluene, xylene, etc., at a temperature of 50° to 80° C. for 4 to 24 hours. Compound XI in turn can be further N-substituted in a conventional manner of alkylation, such as for example by treatment of the sodium salt thereof (from sodium metal or sodium hydride) with an alkyl iodide, e.g. methyliodide, or dimethylsulfate.

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med. 95, 729 (1957)].

The analgesic activity of some of the compounds expressed in a dosage of the compounds which exhibit either (a) a 50% effective dose inhibition (ED$_{50}$) or (b) a percent inhibition is given in Table I.

TABLE I

| Compound | (ED$_{50}$) Subcutaneous Dose in Mg/kg of Body Weight | (ED$_{50}$) Oral Dose in Mg/kg of Body Weight | % (Decrease) | Subcutaneous Dose (Mg/kg) |
|---|---|---|---|---|
| N—[1-(2-phenethyl)piperidin-4-yl]-N—(1H—pyrrol-1-yl)propanamide hydrochloride | 0.35 | 1.4 | — | — |
| N—[1-(2-phenethyl)piperidin-4-yl)]-N—(1H-pyrrol-1-yl)-acetamide hydrochloride | 1.2 | 9.5 | — | — |
| N—[1-(2-phenethyl)piperidin-4-yl]-N—(1H—pyrrol-1-yl)carbamic acid ethyl ester hydrochloride | 2.4 | 5.6 | — | — |
| N—[1-(2-phenethyl)piperidin-4-yl]-N—(1H—pyrrol-1-yl)carbamic acid methyl ester hydrochloride | 0.65 | 7.7 | — | — |
| N—[1-(2-phenethyl)piperidin-4-yl]-N—(1H—pyrrol-1-yl)cyanamide hydrochloride | 2.4 | — | — | — |
| N—{1-[2-(4-chlorophenyl)ethyl]piperidin-4-yl}-N—(1H—pyrrol-1-yl)propanamide | — | — | 76 | 40 |
| N—[1-(n-butyl)piperidin-4-yl]-N—(1H—pyrrol-1-yl)carbamic acid ethyl ester | — | — | 20 | 20 |
| N—[1-(n-butyl)piperidin-4-yl]-N—(1H—pyrrol-1-yl)propanamide maleate | — | — | 45 | 10 |
| 1-(2-phenethyl)-4-(1H—pyrrol-1-yl)aminopiperidine maleate | — | — | 49 | 10 |
| N—{1-[2-(4-methoxyphenyl)ethyl]piperidin-4-yl}-N—(1H—pyrrol-1-yl)propanamide | — | — | 27 | 10 |
| N—{1-[2-(4-methoxyphenyl)ethyl]piperidin-4-yl}-N—(1H—pyrrol-1-yl)cyanamide hydrochloride | — | — | 51 | 10 |
| 1-(2-phenethyl)-4-[N—(n-propyl)-N—(1H—pyrrol-1-yl)]aminopiperidine oxalate | — | — | 53 | 10 |
| N—[1-(2-phenylpropyl)-piperidin-4-yl]-N—(1H—pyrrol-1-yl)propanamide hydrochloride | — | — | 30 | 10 |
| N—[1-(2-phenylpropyl)piperidin-4-yl]-N—(1H—pyrrol-1-yl)carbamic acid ethyl ester | — | — | 42 | 10 |
| N—[1-(2-phenethyl)piperidin-4-yl]-N—(1H—pyrrol-1-yl)acrylamide hydrochloride | — | — | 100 | 10 |
| N—[1-(2-phenethyl)piperidin-4-yl]-N—(1H—pyrrol-1-yl)-N'—methylurea hydrochloride | — | — | 100 | 10 |
| N—[1-(2-phenethyl)piperidin-4-yl]-N—(1H—pyrrol-1-yl)cyclobutanecarboxylic acid amide hydrochloride | — | — | 65 | 10 |
| N—{1-[2-(2-thienyl)ethyl]piperidin-4-yl}-N—(1H—pyrrol-1-yl)carbamic acid ethyl ester hydrochloride | — | — | 54 | 10 |
| N—[1-(2-phenethyl)piperidin-4-yl]-N—(1H—pyrrol-1-yl)propanethioamide hydrochloride | — | — | 99 | 10 |

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the pyrrolylaminopiperidines and related compounds of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the pyrrolylaminopiperidines and related compounds of the invention.

The tablets, pills, capsules, troches and the like may also contain the following adjuvants: a binder such as microcrystalline cellulose, gum tragacanth or gelatin;

an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added to a flavoring agent such as peppermint, methyl salicylate or orange flavoring. When the dosage unit form is a capsule, it may contain, in addition to material of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the pyrrolylaminopiperidines and related compounds of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the pyrrolylaminopiperidine and related compounds of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid, buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade unless indicated otherwise.

EXAMPLE 1

N-(1-Methylpiperidin-4-yl)-N-(1H-pyrrol-1-yl)propanamide maleate

A solution of 1-aminopyrrole (4.2 g, 0.05 mol) and 1-methyl-4-piperidine (6.9 g, 0.06 mol) in cyclohexane was refluxed overnight (about 16 hours) over 4 Å molecular sieves. After 3 hours, an additional 1 g of 1-methyl-4-piperidone was added. The molecular sieves were filtered off and the cyclohexane removed by evaporation under reduced pressure. The resulting oil was dissolved in isopropanol and 5 g of sodium borohydride added. The mixture was stirred at reflux for three hours, then methanol was added, the heat was removed, and stirring continued until the mixture had cooled to room temperature. The solvent was removed by evaporation under reduced pressure to give a residue to which water was added. This mixture was extracted with dichloromethane, the dichloromethane solution was dried with saturated sodium chloride solution and magnesium sulfate, and the dichloromethane evaporated in vacuo to give 7 g (78%) of 1-methyl-4-(1H-pyrrol-1-yl)aminopiperidine. To a cooled solution of 1-methyl-4-(1H-pyrrol-1-yl)aminopiperidine (5.4 g, 0.03 mol) and triethylamine (3.35 g, 0.033 mol) in $CHCl_3$ (100 ml) was added dropwise a solution of propionyl chloride (3.07 g, 0.033 mol) in $CHCl_3$ (100 ml). The reaction mixture was stirred at ice bath temperature for one hour, then at room temperature overnight (about 16 hours). The chloroform solution was washed with water, dried with saturated sodium chloride and magnesium sulfate, and the chloroform removed to give 4.8 g of an oil. The oxalate was formed by adding ethereal oxalic acid but did not crystallize. The resultant oil was basified, extracted with dichloromethane and dried to give 3.2 g of an oil. This oil was chromatographed on a high pressure liquid chromatograph (HPLC) using 1½% diethylamine in acetonitrile. The resultant 1.5 g of free base was converted to the maleate (1.9 g) by adding ethereal maleic acid and recrystallized from absolute ethanol/ether to give 1.8 g, m.p. 146°–147° C. of N-(1-methylpiperidin-4-yl)-N-(1H-pyrrol-1-yl)propanamide maleate. The recovered starting material was reacted again with propionyl chloride (0.7 g) in $CH_2Cl_2$ (20 ml) with sodium bicarbonate (1 g) at room temperature overnight. Work-up gave an oil which was dissolved in ether, and an ether solution of maleic acid added to give the maleate salt. Recrystallization from absolute ethanol/ether gave an additional 1.5 g of product of N-(1-methylpiperidin-4-yl)-N-(1H-pyrrol-1-yl)propanamide maleate, mp 146°–147° C., combined yield 3.3 g (9.39 mmol), 31.3% yield from 1-methyl-4-(1H-pyrrol-1-yl)aminopiperidine.

ANALYSIS: Calculated for $C_{13}H_{21}N_3O \cdot C_4H_4O_4$: 58.09%C; 7.18%H; 11.96%N. Found: 58.29%C; 7.02%H; 12.05%N.

EXAMPLE 2

N-[1-(2-Phenethyl)piperidin-4-yl]-N-(1H-pyrrol-1-yl)propanamide hydrochloride

A solution of 1-aminopyrrole (6 g, 73 mmole) and 1-(2-phenethyl)-4-piperidone (16 g, 80 mmole) in 250 ml benzene was stirred six hours at reflux. The reaction mixture was cooled, filtered and evaporated to 20 g of an oil. This oil was dissolved in 200 ml isopropanol and 50 ml methanol and stirred two hours at reflux with $NaBH_4$ (6 g, 0.16 mole). The reaction mixture was cooled and evaporated to a semi-solid which was stirred with water and extracted with ether. The organic extract was washed with water, saturated NaCl and was dried (anhydrous $MgSO_4$), filtered and evaporated to 20 g of an oil. This oil was purified by HPLC to give 17 g (86%) of an oil comprising 1-(2-phenethyl)-4-(1H-pyrrol-1-yl)aminopiperidine. To a solution of 1-(2-phenethyl)-4-(1H-pyrrol-1-yl)aminopiperidine (4.5 g, 17 mmole) in 150 ml dichloromethane containing sodium bicarbonate (2.8 g, 33 mmole) was added a solution of propionyl chloride (1.8 g, 10 mmole) in 10 ml dichloromethane. After stirring two days at ambient temperature, the reaction mixture was evaporated to an oil that was stirred with water and extracted with ethyl acetate. The organic extract was washed with water and saturated NaCl and was dried (anhydrous $MgSO_4$), filtered and evaporated to 5.4 g of an oil. This oil was converted to the hydrochloride salt by adding ethereal hydrogen chloride and recrystallized from isopropanol/methanol to give 5.1 g (84%) of N-[1-(2-phenethyl)-piperidin-4-yl]-N-(1H-pyrrol-1-yl)propanamide hydrochloride, d 270° C.

ANALYSIS: Calculated for $C_{20}H_{27}N_3O \cdot HCl$: 66.37%C; 7.80%H; 11.61%N. Found: 66.53%C; 7.80%H; 11.58%N.

EXAMPLE 3

N-[1-(2-Phenethyl)piperidin-4-yl]-N-(1H-pyrrol-1-yl)acetamide hydrochloride

To a solution of 1-(2-phenethyl)-4-(1H-pyrrol-1-yl)aminopiperidine of Example 11 (4.5 g, 17 mmole) in 200 ml dichloromethane containing sodium bicarbonate (2.8 g, 33 mmole) was added a solution of acetyl chloride (1.5 g, 19 mmole) in 20 ml dichloromethane. After stirring twenty hours at ambient temperature, the mixture was evaporated to a solid that was stirred with water and extracted with ethyl acetate-ether. The organic extract was washed with water and saturated NaCl and was dried (anhydrous $MgSO_4$), filtered and evaporated to 5.4 g of a solid. This material was converted to the hydrochloride as in Example 2 and recrystallized from isopropanol-methanol to give 4.8 g (83%) of N-[1-(2-phenethyl)piperidin-4-yl]-N-(1H-pyrrol-1-yl)acetamide hydrochloride, d 278° C.

ANALYSIS: Calculated for $C_{19}H_{25}N_3O \cdot HCl$: 65.59%C; 7.53%H; 12.08%N. Found: 65.42%C; 7.48%H; 12.00%N.

EXAMPLE 4

N-[1-(2-Phenethyl)piperidin-4-yl]-N-(1H-pyrrol-1-yl)carbamic acid ethyl ester hydrochloride To a solution of 1-(2-phenethyl)-4-(1H-pyrrol-1-yl)aminopiperidine of Example 11 (4.1 g. 15 mmole) in 150 ml dichloromethane containing sodium bicarbonate (2.6 g, 30 mmole) was added a solution of ethyl chloroformate (1.9 g, 18 mmole) in 20 ml dichloromethane. After stirring twenty hours at ambient temperature, the mixture was evaporated to a solid that was stirred with water and extracted with ethyl acetate-ether. The organic extract was washed with water and saturated NaCl and was dried (anhydrous $MgSO_4$), filtered and evaporated to 5.2 g of a solid. 3.5 g of the solid was converted to the hydrochloride salt as in Example 2 then recrystallized from isopropanol to give 2.6 g (67%) of N-[1-(2-phenethyl)piperidin-4-yl]-N-(1H-pyrrol-1-yl)carbamic acid ethyl ester hydrochloride.

ANALYSIS: Calculated for $C_{20}H_{27}N_3O_2 \cdot HCl$ 63.55%C; 7.47%H; 11.12%N. Found: 63.93%C; 7.58%H; 11.32%N.

EXAMPLE 5

N-[1-(2-Phenethyl)-piperidin-4-yl]-N-(1H-pyrrol-1-yl)carbamic acid methyl ester hydrochloride To a solution of 1-(2-phenethyl)-4-(1H-pyrrol-1-yl)aminopiperidine of Example 11 (4 g, 15 mmole) in 150 ml dichloromethane containing sodium bicarbonate (2.5 g, 30 mmole) was added a solution of methyl chloroformate (1.6 g, 17 mmole) in 20 ml dichloromethane. After stirring twenty hours at ambient temperature, the reaction mixture was evaporated, stirred with water and extracted with ethyl acetate-ether. The organic extract was washed with water, saturated NaCl and was dried (anhydrous $MgSO_4$), filtered and evaporated to an oil (4.7 g) that was purified by HPLC (silica gel, ethyl acetate/hexane/diethylamine-50/50/1) to give 3.7 g (76%) of a solid. This solid was converted to the hydrochloride salt as in Example 2 and recrystallized from isopropanol to give 3.6 g (67%) of N-[1-(2-phenethyl)-piperidin-4-yl]-N-(1H-pyrrol-1-yl)carbamic acid methyl ester hydrochloride, d 222°-223° C.

ANALYSIS: Calculated for $C_{19}H_{25}N_3O_2 \cdot HCl$: 62.71%C; 7.20%H; 11.55%N. Found: 62.46%C; 7.35%H; 11.45%N.

EXAMPLE 6

N-[1-(2-Phenethyl)-piperidin-4-yl]-N-(1H-pyrrol-1-yl)cyanamide hydrochloride

To a solution of 1-(2-phenethyl)-4-(1H-pyrrol-1-yl)aminopiperidine of Example 11, (4 g, 15 mmole) in 150 ml dichloromethane containing 2.5 g (30 mmole) sodium bicarbonate was slowly added a solution of cyanogen bromide (1.8 g, 17 mmole) in 25 ml dichloromethane. After stirring twenty hours at ambient temperature, the reaction mixture was evaporated, stirred with water and extracted into ethyl acetate-ether. The organic extract was washed with water, saturated NaCl and was dried (anhydrous $MgSO_4$), filtered and evaporated to 5 g of an oil. This oil was converted to the hydrochloride salt as in Example 2 and recrystallized twice from isopropanol to give 2.7 g (55%) of N-[1-(2-phenethyl)-piperidin-4-yl]-N-(1H-pyrrol-1-yl)cyanamide hydrochloride, d 211°-212° C.

ANALYSIS: Calculated for $C_{18}H_{22}N_4 \cdot HCl$: 65.34%C; 7.01%H; 16.94%N. Found: 65.04%C; 6.94%H; 17.06%N.

EXAMPLE 7 a. 1-[2-(4-chlorophenyl)ethyl]-4-(1H-pyrrol-1-yl)aminopiperidine

A mixture of 1-[2-(4-chlorophenyl)ethyl]-4-piperidone (8 g, 33.6 mmole) and 1-aminopyrrole (2.7 g, 33.6 mmole) in 100 ml of benzene was stirred at reflux for 6 hours. An additional 0.5 g of 1-aminopyrrole was added and reflux was continued for 2 hours whereafter an additional 0.5 g of 1-aminopyrrole was added and refluxing was continued overnight (about 16 hours). An additional 0.5 g of 1-aminopyrrole was added followed by refluxing for 6 hours. The resultant mixture was evaporated to yield 13 g of an oil. The oil was dissolved in 100 ml of isopropyl alcohol and 25 ml of methanol. To the solution was added $NaBH_4$ (2.6 g, 68 mmole) and the resultant mixture was refluxed for 2 hours. The mixture was cooled, evaporated with ethylacetate/ether. The organic extract was washed with water, dried, filtered and evaporated to yield 12 g of an oil. The oil was purified by high pressure liquid chromatography (silica, 1% ethanol/ethylacetate) to give 9.6 g (94%) of an oil of 1-[2-(4-chlorophenyl)ethyl]-4-(1H-pyrrol-1-yl)aminopiperidine which solidified at room temperature upon standing.

b. N-{1-[2-(4-Chlorophenyl)ethyl]-piperidin-4-yl}-N-(1H-pyrrol-1-yl)carbamic acid ethyl ester hydrochloride To a solution of 1-[2-(4-chlorophenyl)ethyl]-4-(1H-pyrrol-1-yl)aminopiperidine of Example 7a, (3.6 g, 12 mmole) in 100 ml dichloromethane containing sodium bicarbonate (2.5 g, 30 mmole) was added a solution of ethyl chloroformate (1.6 g, 15 mmole) in 20 ml of dichloromethane. The reaction mixture was stirred three hours at ambient temperature, then was evaporated, stirred with water and extracted with ethyl acetate-ether. The organic extracts were washed with water, saturated NaCl and were dried (anhydrous $MgSO_4$), filtered and evaporated to 4 g of an oil. This oil was purified by HPLC (silica gel; dichloromethane/ethyl acetate/diethylamine:100/20/1) to give 3.4 g of a solid. This material was converted to the hydrochloride salt as in Example 2 and recrystallized from isopropanol to give 2.8 g (58%) of N-{1-[2-(4-chlorophenyl)ethyl]-piperidin-4-yl}-N-(1H-pyrrol-1-yl)carbamic acid ethyl ester hydrochloride, d 253°–254° C.

ANALYSIS: Calculated for $C_{20}H_{26}ClN_3O_2 \cdot HCl$: 58.25%C; 6.60%H; 10.19%N. Found: 58.44%C; 6.58%H; 10.28%N.

EXAMPLE 8

N-{1-[2-(4-Chlorophenyl)ethyl]piperidin-4-yl}-N-(1H-pyrrol-1-yl)propanamide

To a solution of 1-[2-(4-chlorophenyl)ethyl]-4-(1H-pyrrol-1-yl)aminopiperidine of Example 7a, (5 g, 16 mmole) in 150 ml dichloromethane containing sodium bicarbonate (3 g, 36 mmole) was added a solution of propionyl chloride (1.7 g, 18 mmole) in 20 ml dichloromethane. After stirring four hours at ambient temperature, the reaction mixture was washed with water, saturated sodium chloride and was dried (anhydrous $MgSO_4$), filtered and evaporated to give 6 g of a solid. This material was purified by HPLC (silica gel, 20% ethyl acetate/dichloromethane) to give 3.6 g (61%) of a solid, mp 80°–85° C. This was recrystallized from isopropyl ether/petroleum ether (1:1) to give 2.5 g (42%) of N-{1-[2-(4-chlorophenyl)ethyl]piperidin-4-yl}-N-(1H-pyrrol-1-yl)propanamide, mp 85°–86° C.

ANALYSIS: Calculated for $C_{20}H_{26}ClN_3O$: 66.74%C; 7.28%H; 11.68%N. Found: 66.54%C; 7.11%H; 12.00%N.

EXAMPLE 9 a. 1-(n-Butyl)-4-(1H-pyrrol-1-yl)aminopiperidine

A solution of 1-butyl-4-piperidone (6.2 g, 40 mmole) and 1-aminopyrrole (3.3 g, 40 mmole) in 100 ml of toluene was stirred at reflux overnight (about 16 hours). The mixture was cooled and then evaporated to an oil, which in turn was dissolved in 75 ml of isopropanol, and 22 ml of ethanol. To the solution was added $NaBH_4$ (3.8 g, 100 mmole). The mixture was stirred at 70° C. for 2 hours and then evaporated, stirred with water and extracted with ethyl acetate-ether. The organic extract was washed with water and saturated NaCl solution, dried (anhydrous $MgSO_4$), filtered and evaporated to 13 g of an oil. This oil was purified by high pressure liquid chromatography (silica, 1% diethylamine/ethyl acetate) to give 8.2 g of an oil of 1-(n-butyl)-4-(1H-pyrrol-1-yl)aminopiperidine.

b. N-[1-(n-Butyl)piperidin-4-yl]-N-(1H-pyrrol-1-yl)carbamic acid ethyl ester

To a solution of 1-(n-butyl)-4-(1H-pyrrol-1-yl)aminopiperidine of Example 9a, (4 g, 18 mmole) in 100 ml dichloromethane containing sodium bicarbonate (3 g, 36 mmole) was added a solution of ethyl chloroformate (2.3 g, 20 mmole) in 20 ml dichloromethane. After stirring three hours at ambient temperature the reaction mixture was washed with water and extracted with ethyl acetate. The organic extract was washed with water and saturated NaCl and was dried (anhydrous $MgSO_4$), filtered and evaporated to give 4.8 g of an oil. This oil was purified by HPLC (silica gel, ethyl acetate) to give 3.3 g (62%) of an oil. This oil was distilled to give 2.3 g (43%) of N-[1-(n-butyl)piperidin-4-yl]-N-(1H-pyrrol-1-yl)carbamic acid ethyl ester (b.p. 130°–140° C. @ 0.2 mm; m.p. 42°–43° C.).

ANALYSIS: Calculated for $C_{16}H_{27}N_3O_2$: 65.49%C; 9.28%H; 14.32%N. Found: 65.26%C; 9.04%H; 14.05%N.

EXAMPLE 10

N-[1-(n-Butyl)piperidin-4-yl]-N-(1H-pyrrol-1-yl)propanamide maleate

To a solution of 1-(n-butyl)-4-(1H-pyrrol-1-yl)aminopiperidine of Example 9a, (3.5 g, 16 mmole) in 150 ml dichloromethane containing sodium bicarbonate (4 g, 48 mmole) was added a solution of propionyl chloride (1.6 g, 17 mmole) in 25 ml dichloromethane. After stirring five hours at ambient temperature, the reaction mixture was evaporated, stirred with water and extracted with ether. The organic extract was washed with water, saturated NaCl and was dried (anhydrous $MgSO_4$), filtered and evaporated to 4 g of an oil. This oil was purified by HPLC (silica, 20% ethyl acetate in dichloromethane) to give 3.4 g (78%) of an oil. This oil was converted to the maleate salt as in Example 1 and recrystallized from isopropanol-ether to give 4 g (64%) of N-[1-(n-butyl)piperidin-4-yl]-N-(1H-pyrrol-1-yl)propanamide maleate, mp 131°–132° C.

ANALYSIS: Calculated for $C_{16}H_{27}N_3O \cdot C_4H_4O_4$: 61.05%C; 7.94%H; 10.68%N. Found: 61.14%C; 7.91%H; 10.66%N.

EXAMPLE 11

1-(2-Phenethyl)-4-(1H-pyrrol-1-yl)aminopiperidine maleate

A mixture of 1-($\beta$-phenethyl)-4-piperidone (12.4 g, 61 mmole) and 1-aminopyrrole (5 g, 61 mmole) in 100 ml benzene was stirred seven hours at reflux. After cooling, the mixture was evaporated, dissolved in 100 ml isopropanol and 25 ml methanol, and to this solution was added sodium borohydride (4.6 g, 121 mmole). The mixture stirred two hours at 70° C. then was cooled, evaporated, stirred with water and extracted into ethyl acetate-ether. The organic extract was washed with water, saturated NaCl and was dried (anhydrous $MgSO_4$), filtered and evaporated to 17 g of an oil. This oil was purified by HPLC (silica, ethyl acetate) to give 14 g (85%) of a solid, mp 45°–47° C. Two grams of this material was converted to the maleate salt as in Example 1 and recrystallized from isopropanol-ether to give 2.5 g of 1-(2-phenethyl)-4-(1H-pyrrol-1-yl)aminopiperidine maleate, mp 147°–148° C.

ANALYSIS: Calculated for $C_{17}H_{23}N_3 \cdot C_4H_4O_4$: 65.43%C; 7.06%H; 10.90%N. Found: 65.29%C; 7.07%H; 10.88%N.

EXAMPLE 12 a. 1-[2-(4-Methoxyphenyl)ethyl]-4-(1H-pyrrol-1-yl)aminopiperidine

A solution of 1-[2-(4-methoxyphenyl)ethyl-4-piperidone (15 g, 64 mmole) and 1-aminopyrrole (6 g, 73 mmole) in 125 ml of benzene was stirred at 120° C. for 20 hours. The resultant solution was evaporated, dissolved in 125 ml of isopropanol and 50 ml of methanol and then $NaBH_4$ (6 g, 158 mmole) was added. The resultant mixture was stirred 3 hours at 75° C., cooled, evaporated, stirred with water and then extracted with ethyl acetate-ether. The organic extract was washed with water and saturated NaCl solution, dried, (anhydrous $MgSO_4$), filtered and evaporated to 19.7 g of an oil. This oil was purified by high pressure liquid chromatography (silica, 3% methanol/dichloromethane) to give 14.7 g (76.6%) of a solid. 0.5 g of this solid was recrystallized from isopropyl ether to give 0.1 g of 1-[2-(4-methoxyphenyl)ethyl]-4-(1H-pyrrol-1-yl)aminopiperidine.

ANALYSIS: Calculated for $C_{18}H_{25}N_3O$: 72.20%C; 8.42%H; 14.04%N. Found: 72.51%C; 8.40%H; 14.10%N.

b. N-{1-[2-(4-Methoxyphenyl)ethyl]piperidin-4-yl}-N-(1H-pyrrol-1-yl)propanamide

To a solution of 1-[2-(4-methoxyphenyl)ethyl]-4-(1H-pyrrol-1-yl)aminopiperidine of Example 12a, (3.6 g, 12 mmole) in 100 ml dichloromethane containing sodium bicarbonate (2 g, 24 mmole) was added a solution of propionyl chloride (1.1 g, 12 mmole) in 20 ml dichloromethane. After stirring two hours at ambient temperature, the reaction mixture was evaporated, stirred with water and extracted into ethyl acetate-ether. The organic extract was washed with water and saturated NaCl and was dried (anhydrous MgSO₄), filtered and evaporated to give 4 g of a solid. This material was recrystallized from isopropyl ether-petroleum ether (1:1) to give 2.8 g (65%) of N-{1-[2-(4-methoxyphenyl)ethyl]piperidin-4-yl}-N-(1H-pyrrol-1-yl)propanamide, mp 83°-84° C.

ANALYSIS: Calculated for $C_{21}H_{29}N_3O_2$: 70.95%C; 8.22%H; 11.82%N. Found: 70.98%C; 8.24%H; 11.76%N.

EXAMPLE 13

N-{1-[2-(4-Methoxyphenyl)ethyl]piperidin-4-yl})-N-(1H-pyrrol-1-yl)cyanamide hydrochloride To a solution of 1-[2-(4-methoxyphenyl)ethyl]-4-(1H-pyrrol-1-yl)aminopiperidine of Example 12a (4 g, 13.4 mmole) in 150 ml dichloromethane containing sodium bicarbonate (3.4 g, 40 mmole) was added a solution of cyanogen bromide (1.6 g, 14.7 mmole) in 25 ml dichloromethane. After stirring twenty hours at ambient temperature, the reaction mixture was evaporated, stirred with water and extracted with ether. The organic extract was washed with water and saturated NaCl and was dried (anhydrous MgSO₄), filtered and evaporated to 5 g of an oil. The oil was converted to the hydrochloride salt as in Example 2 and was recrystallized from isopropanol-ether to give 2.8 g (58%) N-{1-[2-(4-methoxyphenyl)ethyl]piperidin-4-yl}-N-(1H-pyrrol-1-yl)cyanamide hydrochloride, d 227°-229° C.

ANALYSIS: Calculated for $C_{19}H_{24}N_4O.HCl$: 63.23%C; 6.98%H; 15.53%N. Found: 63.17%C; 6.92%H; 15.42%N.

EXAMPLE 14

1-(2-Phenethyl)-4-[N-(n-propyl)-N-(1H-pyrrol-1-yl)]aminopiperidine oxalate

To a solution of borane-tetrahydrofuran (THF) complex (0.97 M in THF, 86 mmole, 86 ml), cooled with an ice bath, was slowly added a solution of N-[1-(2-phenethyl)piperidin-4-yl]-N-(1H-pyrrol-1-yl)propanamide of Example 2, (7 g, 22 mmole) in 25 ml tetrahydrofuran. After stirring three hours at ambient temperature the reaction mixture was cooled and excess borane was quenched by slow addition of 3 N HCl. The mixture was then basified with sodium carbonate and the oil which separated was extracted with ethyl acetate-ether. The organic extract was washed with water and saturated NaCl and was dried (anhydrous MgSO₄), filtered and evaporated to give 8 g of a solid, mp 121°-123° C. A mixture of this solid in 175 ml 3 N HCl was stirred three hours at 105° C., then was cooled, diluted with water and basified with sodium carbonate. The oil which separated was extracted with ethyl-acetate ether. The organic extract was washed with water, saturated NaCl and was dried (anhydrous MgSO₄), filtered and evaporated to give 7 g of an oil. This oil was purified by HPLC (silica, ethyl acetate) to give 5 g (75%) of an oil. This oil was converted to the oxalate salt as in Example 1 and was recrystallized from isopropanol to give 5.5 g (64%) of 1-(2-phenethyl)-4-[N-(n-propyl)-N-(1-H-pyrrol-1-yl)]aminopiperidine oxalate, d 188°-190° C.

ANALYSIS: Calculated for $C_{20}H_{29}N_3.C_2H_2O_4$: 65.81%C; 7.78%H; 10.47%N. Found: 65.88%C; 7.71%H; 10.36%N.

EXAMPLE 15 a. 1-(2-Phenylpropyl)-4-(1H-pyrrol-1-yl)-aminopiperidine

A solution of 1-aminopyrrole (6 g, 73.1 mmole) and 1-(2-phenylpropyl)-4-piperidone (13.8 g, 63.5 mmole) in 100 ml of benzene was stirred at reflux for 3 hours. The resultant mixture was evaporated, dissolced in 100 ml of isopropanol and 25 ml of ethanol and to the resultant solution was added NaBH₄ (4.8 g, 0.13 mole). The resultant mixture was stirred 2 hours at 70° C. and then kept at room temperature for 3 days. The mixture was evaporated, stirred with water and extracted with ether. The organic extract was washed with water and saturated NaCl solution and was dried (anhydrous MgSO₄), filtered and evaporated to 18 g of an oil. This oil was purified by high pressure liquid chromatography (silica, 3% methanol/dichloromethane) to give 14 g (77.8%) of an oil which on cooling yielded a solid of 1-(2-phenylpropyl)-4-(1H-pyrrol-1-yl)aminopiperidine, m.p. 72°-74° C.

b. N-[1-(2-Phenylpropyl)piperidin-4-yl]-N-(1H-pyrrol-1-yl)propanamide hydrochloride To a solution of 1-(2-phenylpropyl)-4-(1H-pyrrol-1-yl)aminopiperidine of Example 15a, (3.5 g, 12.3 mmole) in 100 ml dichloromethane containing sodium bicarbonate (3.1 g, 37 mmole) was added a solution of propionyl chloride (1.3 g, 13.6 mmole) in 20 ml dichloromethane. After stirring six hours at ambient temperature the reaction mixture was evaporated, stirred with water and extracted into ether. The organic extract was washed with water, saturated sodium chloride and was dried (anhydrous MgSO₄), filtered and evaporated to give 5 g of an oil. This oil was converted to the hydrochloride salt as in Example 2 and was recrystallized from isopropanol-ether to give 4.1 g (89%) of N-[1-(2-phenylpropyl)piperidin-4-yl]-N-(1H-pyrrol-1-yl)propanamide hydrochloride, d 258°-259° C.

ANALYSIS: Calculated for $C_{21}H_{29}N_3O.HCl$: 67.09%C; 8.04%H; 11.18%N. Found: 67.14%C; 7.98%H; 11.15%N.

EXAMPLE 16

N-[1-(2-Phenylpropyl)piperidin-4-yl]-N-(1H-pyrrol-1-yl)carbamic acid ethyl ester hydrochloride To a solution of 1-(2-phenylpropyl)-4-(1H-pyrrol-1-yl)aminopiperidine of Example 15a (3.5 g, 13.2 mmole) in 100 ml dichloromethane containing sodium bicarbonate (4 g, 48 mmole) was added a solution of ethyl chloroformate (1.6 g, 15 mmole) in 20 ml dichloromethane. After stirring twenty hours at ambient temperature, the reaction mixture was evaporated, stirred with water and extracted into ether. The organic extract was washed with water, saturated NaCl and was dried (anhydrous MgSO$_4$), filtered and evaporated to give 4.5 g of an oil. The oil was purified by HPLC (silica gel, ethyl acetate) to give 3.6 g (82%) of an oil. This oil was converted to the hydrochloride salt as in Example 2 then recrystallized from isopropanol-ether to give 3.1 g (64%) of N-[1-(2-phenylpropyl)piperidin-4-yl]-N-(1H-pyrrol-1-yl)carbamic acid ethyl ester hydrochloride.

ANALYSIS: Calculated for C$_{21}$H$_{29}$N$_3$O$_2$HCl: 64.35%C; 7.72%H; 10.72%N. Found: 64.26%C; 7.76%H; 10.54%N.

EXAMPLE 17

N-[1-(2-Phenethyl)piperidin-4-yl]-N-(1H-pyrrol-1-yl)carbamic acid-(n-butyl)-ester hydrochloride To a solution of 1-(2-phenethyl)-4-(1H-pyrrol-1-yl)aminopiperidine of Example 11 (5 g, 10 mmole) in 150 ml dichloromethane containing sodium bicarbonate (3 g, 36 mmole) was added a solution of butyl chloroformate (2.8 g, 20 mmole) in 20 ml dichloromethane. After stirring twenty hours at ambient temperature, the reaction mixture was evaporated, stirred with water and extracted with ether. The organic extract was washed with water and saturated sodium chloride and was dried (anhydrous MgSO$_4$), filtered and evaporated to give 7 g of an oil. This oil was purified by HPLC (silica gel, 10% ethyl acetate in dichloromethane) to give 5.2 g (75%) of a solid mp 60° C. This material was converted to the hydrochloride salt as in Example 2 and was recrystallized from isopropanol-ether to give 3.2 g (42%) of N-[1-(2-phenethyl)piperidin-4-yl]-N-(1H-pyrrol-1-yl)carbamic acid-(n-butyl)-ester hydrochloride, d 216°-217° C.

ANALYSIS: Calculated for C$_{22}$H$_{31}$N$_3$O$_2$.HCl: 65.09%C; 7.95%H; 10.35%N. Found: 65.37%C; 7.96%H; 10.38%N.

EXAMPLE 18

N-[1-(2-Phenethyl)piperidin-4-yl]-N-(1H-pyrrol-1-yl)acrylamide hydrochloride

To a solution of 1-(2-phenethyl)-4-(1H-pyrrol-1-yl)aminopiperidine of Example 11 (4 g, 14.8 mmole) in 150 ml dichloromethane containing sodium bicarbonate (4 g, 48 mmole) was added a solution of acryloyl chloride (1.5 g, 17 mmole) in 20 ml dichloromethane. After stirring twenty hours at ambient temperature the reaction mixture was evaporated, stirred with water and extracted with ethyl acetate-ether. The organic extract was washed with water and saturated sodium chloride and was dried (anhydrous MgSO$_4$), filtered and evaporated to 4.8 g of a solid. This material was purified by HPLC (silica gel, 20% ethyl acetate in dichloromethane) to give 3.3 g (69%) of a solid. This material was converted to the hydrochloride salt as in Example 2 and was recrystallized from isopropanol to give 3.2 g (60%) of N-[1-(2-phenethyl)piperidin-4-yl]-N-(1H-pyrrol-1-yl)acrylamide hydrochloride, d 278°-279° C.

ANALYSIS: Calculated for C$_{20}$H$_{25}$N$_3$O.HCl: 66.74%C; 7.28%H; 11.68%N. Found: 66.64%C; 7.28%H; 11.76%N.

EXAMPLE 19

N-[1-(2-Phenethyl)piperidin-4-yl]-N-(1H-pyrrol-1-yl)-N'-methylurea hydrochloride A solution of 1-(2-phenethyl)-4-(1H-pyrrol-1-yl)aminopiperidine of Example 11 (3.5 g, 13 mmole) and methyl isocyanate (0.8 g, 14 mmole) in 125 ml benzene was stirred at 50° C. for four hours, then was cooled and evaporated to a solid. This material was dissolved in warm isopropanol and converted to the hydrochloride salt as in Example 2. Upon cooling, the product precipitated and was collected to give 3.6 g (76%) of a solid, d 250°-251° C. This material was again recrystallized from isopropanol to give 3.2 g (68%) of N-[1-(2-phenethyl)piperidin-4-yl]-N-(1H-pyrrol-1-yl)-N'-methylurea hydrochloride, d 252°-253° C.

ANALYSIS: Calculated for C$_{19}$H$_{26}$N$_4$O.HCl: 62.88%C; 7.50%H; 15.44%N. Found: 62.99%C; 7.55%H; 15.31%N.

EXAMPLE 20 a. 1-[2-(2-Thienyl)ethyl]-4-(1H-pyrrol-1-yl)aminopiperidine

A solution of 1-(2-thienylethyl)-4-piperidone (24.6 g, 0.12 mole) and 1-aminopyrrole (12 g, 0.15 mole) in 200 ml of benzene was stirred at reflux for 4 hours. The resultant mixture was cooled and evaporated to an oil which in turn was dissolved in 200 ml of isopropanol and 50 ml of methanol. To the resultant solution was added NaBH$_4$ (9.1 g, 0.24 mole). The mixture was stirred at 80° C. for 2 hours, cooled, evaporated, stirred with water and then extracted with ethyl acetate-ether. The organic extract was washed twice with water and saturated NaCl solution and was dried (anhydrous MgSO$_4$), filtered and evaporated to 33 g of an oil of 1-[2-(2-thienyl)ethyl]-4-(1H-pyrrol-1-yl)aminopiperidine.

b. N-{1-[2-(2-Thienyl)ethyl]piperidin-4-yl}-N-(1H-pyrrol-1-yl)propanamide hydrochloride To a solution of 1-[2-(2-thienyl)ethyl]-4-(1H-pyrrol-1-yl)aminopiperidine of Example 20a (5 g, 18 mmole) in 150 ml dichloromethane containing sodium bicarbonate (5 g, 60 mmole) was added a solution of propionyl chloride (2 g, 22 mmole) in 20 ml dichloromethane. After stirring two hours at ambient temperature, the reaction mixture was evaporated, stirred with water and extracted into ethyl acetate-ether. The organic extract was washed with water and saturated sodium chloride and was dried (anhydrous MgSO$_4$), filtered and evaporated to give 6.2 g of an oil. This oil was purified by HPLC (silica gel, 20% ethyl acetate in dichloromethane) to give 4 g (67%) of an oil. This oil was converted to the hydrochloride salt as in Example 2 and was recrystallized from isopropanol to give 4.3 g (63%) of N-{1-[2-(2-thienyl)ethyl]piperidin-4-yl}-N-(1H-pyrrol-1-yl) propanamide hydrochloride, d 276°-277° C.

ANALYSIS: Calculated for C$_{18}$H$_{25}$N$_3$OS.HCl: 58.75%C; 7.12%H; 11.42%N. Found: 58.82%C; 7.16%H; 11.17%N.

EXAMPLE 21

N-[2-(2-Phenethyl)piperidin-4-yl]-N-(1H-pyrrol-1-yl)cyclobutanecarboxylic acid amide hydrochloride To a solution of 1-(2-phenethyl)-4-(1H-pyrrol-1-yl)aminopiperidine of Example 11 (4.4 g, 16 mmole) in 150 ml dichloromethane containing sodium bicarbonate (5 g, 60 mmole) was added a solution of cyclobutanecarboxylic acid chloride (2.1 g, 18 mmole) in 25 ml dichloromethane. After stirring twenty hours at ambient temperature, the reaction mixture was evaporated, stirred with water and extracted with ether. The organic extract was washed with water and saturated sodium chloride and was dried (anhydrous MgSO$_4$), filtered and evaporated to 6.5 g of a solid. This material was purified by HPLC (silica gel, 25% ethyl acetate in dichloromethane) to give 5.2 g (91%) of a solid mp 103°–105° C. This material was converted to the hydrochloride salt as in Example 2 in warm isopropanol and, upon cooling, yielded 5.0 g (79%) of N-[1-(2-phenethyl)piperidin-4-yl]-N-(1H-pyrrol-1-yl)cyclobutanecarboxylic acid amide hydrochloride, d 264°–265° C.

ANALYSIS: Calculated for $C_{22}H_{29}N_3O.HCl$: 68.11%C; 7.79%H; 10.83%N. Found: 68.24%C; 7.68%H; 10.78%N.

EXAMPLE 22

N-{1-[2-(2-Thienyl)ethyl]piperidin-4-yl}-N-(1H-pyrrol-1-yl) carbamic acid ethyl ester hydrochloride To a solution of 1-[2-(2-thienyl)ethyl]-4-(1H-pyrrol-1-yl)aminopiperidine of Example 20a (5 g, 18 mmole) in 150 ml dichloromethane containing sodium bicarbonate (5 g, 60 mmole) was added a solution of ethyl chloroformate (2.4 g, 22 mmole) in 20 ml dichloromethane. After stirring twenty hours at ambient temperature, the reaction mixture was evaporated, stirred with water and extracted with ethyl acetate-ether. The organic extract was washed with water and saturated sodium chloride and was dried (anhydrous $MgSO_4$), filtered and evaporated to give 6.3 g of a solid. This solid was purified by HPLC (silica gel, 20% ethyl acetate in dichloromethane) to give 4 g (64%) of a solid mp 104°–106° C. This material was converted to the hydrochloride salt as in Example 2 and was recrystallized from isopropanol to give 4 g (57%) of N-{1-[2-(2-thienyl)ethyl]piperidin-4-yl}-N-(1H-pyrrol-1-yl) carbamic acid ethyl ester hydrochloride, d 212°–213° C.

ANALYSIS: Calculated for $C_{18}H_{25}N_3O_2S.HCl$: 56.31%C; 6.83%H; 10.95%N. Found: 56.22%C; 6.85%H; 10.86%N.

EXAMPLE 23

N-[1-(2-Phenethyl)piperidin-4-yl]-N-(1H-pyrrol-1-yl)propanethioamide hydrochloride A mixture of N-[1-(2-phenethyl)piperidin-4-yl]-N-(1H-pyrrol-1-yl)propanamide of Example 2 (4.2 g, 13 mmole) and p-methoxyphenylthionophosphine sulfide dimer (2.2 g, 6.5 mmole) in 25 ml dioxane was stirred at 70° C. for two hours then was cooled, stirred with 500 ml water and was extracted with ethyl acetate. The organic extract was washed with water and saturated NaCl and was dried (anhydrous $MgSO_4$), filtered and evaporated to 6 g of an oil. This oil was converted to the hydrochloride salt as in Example 2 and was recrystallized from isopropanol to give 2.1 g (43%) of N-[1-(2-phenethyl)piperidin-4-yl]-N-(1H-pyrrol-1-yl) propanethioamide hydrochloride, d 252°–253° C.

ANALYSIS: Calculated for $C_{20}H_{27}N_3S.HCl$: 63.55%C; 7.47%H; 11.12%N. Found: 63.65%C; 7.39%H; 11.01%N.

We claim:

1. A compound having the formula

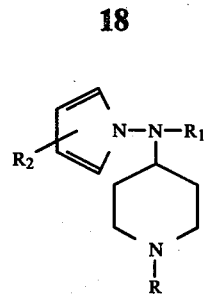

where R is hydrogen, loweralkyl, Arloweralkyl of the formula

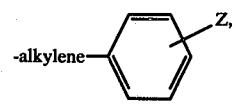

where Z is hydrogen, loweralkyl, loweralkoxy, halogen, $CF_3$, $NO_2$, $NH_2$; cycloalkylloweralkyl, loweralkenyl and thienylloweralkyl; $R_1$ is hydrogen, loweralkyl, loweralkylcarbonyl, loweralkoxycarbonyl, loweralkylthiocarbonyl, cyano, loweralkylaminocarbonyl, diloweralkylaminocarbonyl, cycloalkylcarbonyl, cycloalkylloweralkylcarbonyl and loweralkenylcarbonyl; $R_2$ is hydrogen, halogen and —$CH_3$; and the pharmaceutically acceptable addition salts thereof.

2. The compound as defined in claim 1 wherein R is

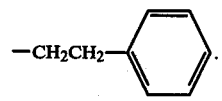

3. The compound as defined in claim 2 wherein $R_1$ is lower alkoxycarbonyl, loweralkylcarbonyl and cyano.

4. The compound as defined in claim 3 wherein $R_2$ is hydrogen.

5. The compound as defined in claim 1 which is N-(1-methylpiperidin-4-yl)-N-(1H-pyrrol-1-yl)propanamide or a pharmaceutically acceptable addition salt thereof.

6. The compound as defined in claim 1 which is N-[1-(2-phenethyl)piperidin-4-yl]-N-(1H-pyrrol-1-yl)propanamide or a pharmaceutically acceptable addition salt thereof.

7. The compound as defined in claim 1 which is N-[1-(2-phenylethyl)piperidin-4-yl]-N-(1H-pyrrol-1-yl)acetamide or a pharmaceutically acceptable addition salt thereof.

8. The compound as defined in claim 1 which is N-[1-(2-phenylethyl)piperidin-4-yl]-N-(1H-pyrrol-1-yl) carbamic acid ethyl ester or a pharmaceutically acceptable addition salt thereof.

9. The compound as defined in claim 1 which is N-[1-(2-phenylethyl)piperidin-4-yl]-N-(1H-pyrrol-1-yl) carbamic acid methyl ester or a pharmaceutically acceptable addition salt thereof.

10. The compound as defined in claim 1 which is N-[1-(2-phenethyl)piperidin-4-yl]-N-(1H-pyrrol-1-yl) cyanamide or a pharmaceutically acceptable addition salt thereof.

11. The compound as defined in claim 1 which is N-{1-[2-(4-chlorophenyl)ethyl]-piperidin-4-yl}-N-(1H-pyrrol-1-yl)carbamic acid ethyl ester or a pharmaceutically acceptable addition salt thereof.

12. The compound as defined in claim 1 which is N-{1-[2-(4-chlorophenyl)ethyl]piperidin-4-yl}-N-(1H-pyrrol-1-yl)propanamide or a pharmaceutically acceptable addition salt thereof.

13. The compound as defined in claim 1 which is N-[1-(n-butyl)piperidin-4-yl]-N-(1H-pyrrol-1-yl)carbamic acid ethyl ester or a pharmaceutically acceptable addition salt thereof.

14. The compound as defined in claim 1 which is N-[1-(n-butyl)piperidin-4-yl]-N-(1H-pyrrol-1-yl)propanamide or a pharmaceutically acceptable addition salt thereof.

15. The compound as defined in claim 1 which is 1-(2-phenethyl)-4-(1H-pyrrol-1-yl)aminopiperidine or a pharmaceutically acceptable addition salt thereof.

16. The compound as defined in claim 1 which is N-{1-[2-(4-methoxyphenyl)ethyl]piperidin-4-yl}-N-(1H-pyrrol-1-yl)propanamide or a pharmaceutically acceptable addition salt thereof.

17. The compound as defined in claim 1 which is N-{1-[2-(4-methoxyphenyl)ethyl]piperidin-4-yl}-N-(1H-pyrrol-1-yl)cyanamide or a pharmaceutically acceptable addition salt thereof.

18. The compound as defined in claim 1 which is 1-(2-phenethyl)-4-[N-(n-propyl)-N-(1H-pyrrol-1-yl)]aminopiperidine or a pharmaceutically acceptable addition salt thereof.

19. The compound as defined in claim 1 which is N-[1-(2-phenylpropyl)piperidin-4-yl]-N-(1H-pyrrol-1-yl)propanamide or a pharmaceutically acceptable addition salt thereof.

20. The compound as defined in claim 1 which is N-[1-(2-phenylpropyl)piperidin-4-yl]-N-(1H-pyrrol-1-yl) carbamic acid ethyl ester or a pharmaceutically acceptable addition salt thereof.

21. The compound as defined in claim 1 which is N-[1-(2-phenethyl)piperidin-4-yl]-N-(1H-pyrrol-1-yl)carbamic acid-(n-butyl)ester or a pharmaceutically acceptable addition salt thereof.

22. The compound as defined in claim 1 which is N-[1-(2-phenethyl)piperidin-4-yl]-N-(1H-pyrrol-1-yl)acrylamide or a pharmaceutically acceptable addition salt thereof.

23. The compound as defined in claim 1 which is N-[1-(2-phenethyl)piperidin-4-yl]-N-(1H-pyrrol-1-yl)-N'-methylurea or a pharmaceutically acceptable addition salt thereof.

24. The compound as defined in claim 1 which is N-{1-[2-(2-thienyl)ethyl]piperidin-4-yl}-N-(1H-pyrrol-1-yl)propanamide or a pharmaceutically acceptable addition salt thereof.

25. The compound as defined in claim 1 which is N-[1-(2-phenethyl)piperidin-4-yl]-N-(1H-pyrrol-1-yl) cyclobutanecarboxylic acid amide or a pharmaceutically acceptable addition salt thereof.

26. The compound as defined in claim 1 which is N-{1-[2-(2-thienyl)ethyl]piperidin-4-yl}-N-(1H-pyrrol-1-yl)carbamic acid ethyl ester or a pharmaceutically acceptable addition salt thereof.

27. The compound as defined in claim 1 which is N-[1-(2-phenethyl)piperidin-4-yl]-N-(1H-pyrrol-1-yl) propanethioamide or a pharmaceutically acceptable addition salt thereof.

28. An analgesic composition which comprises an effective pain alleviating amount of a compound of the formula

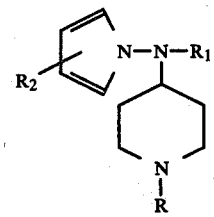

where R is hydrogen, loweralkyl, Arloweralkyl of the formula

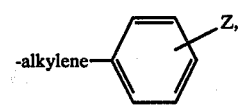

where Z is hydrogen, loweralkyl, loweralkoxy, halogen, CF₃, NO₂, NH₂; cycloalkylloweralkyl, loweralkenyl and thienylloweralkyl; R₁ is hydrogen, loweralkyl, loweralkylcarbonyl, loweralkoxycarbonyl, loweralkylthiocarbonyl, cyano, loweralkylaminocarbonyl, diloweralkylaminocarbonyl, cycloalkylcarbonyl, cycloalkylloweralkylcarbonyl and loweralkenylcarbonyl; R₂ is hydrogen, halogen and —CH₃; and the pharmaceutically acceptable addition salts thereof.

29. The composition as defined in claim 28 wherein R is

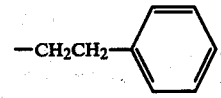

30. The composition as defined in claim 29 wherein R₁ is lower alkoxycarbonyl, loweralkylcarbonyl and cyano.

31. The composition as defined in claim 30 wherein R₂ is hydrogen.

32. The composition as defined in claim 28 which comprises N-(1-methylpiperidin-4-yl)-N-(1H-pyrrol-1-yl)propanamide or a pharmaceutically acceptable salt thereof.

33. The composition as defined in claim 28 which comprises N-[1-(2-phenethyl)piperidin-4-yl]-N-(1H-pyrrol-1-yl)propanamide or a pharmaceutically acceptable salt thereof.

34. The composition as defined in claim 28 which comprises N-[1-(2-phenylethyl)piperidin-4-yl]-N-(1H-pyrrol-1-yl)acetamide or a pharmaceutically acceptable salt thereof.

35. The composition as defined in claim 28 which comprises N-[1-(2-phenylethyl)piperidin-4-yl]-N-(1H-pyrrol-1-yl) carbamic acid ethyl ester or a pharmaceutically acceptable salt thereof.

36. The composition as defined in claim 28 which comprises N-[1-(2-phenylethyl)piperidin-4-yl]-N-(1H-pyrrol-1-yl) carbamic acid methyl ester or a pharmaceutically acceptable salt thereof.

37. The composition as defined in claim 28 which comprises N-[1-(2-phenethyl)piperidin-4-yl]-N-(1H-pyrrol-1-yl) cyanamide or a pharmaceutically acceptable salt thereof.

38. The composition as defined in claim 28 which comprises N-{1-[2-(4-chlorophenyl)ethyl]piperidin-4- yl}-N-(1H-pyrrol-1-yl)carbamic acid ethyl ester or a pharmaceutically acceptable salt thereof.

39. The composition as defined in claim 28 which comprises N-{1-[2-(4-chlorophenyl)ethyl]piperidin-4-yl}-N-(1H-pyrrol-1-yl)propanamide or a pharmaceutically acceptable salt thereof.

40. The composition as defined in claim 28 which comprises N-[1-(n-butyl)piperidin-4-yl]-N-(1H-pyrrol-1-yl)carbamic acid ethyl ester or a pharmaceutically acceptable salt thereof.

41. The composition as defined in claim 28 which comprises N-[1-(n-butyl)piperidin-4-yl]-N-(1H-pyrrol-1-yl) propanamide or a pharmaceutically acceptable salt thereof.

42. The composition as defined in claim 28 which comprises 1-(2-phenethyl)-4-(1H-pyrrol-1-yl)aminopiperidine or a pharmaceutically acceptable salt thereof.

43. The composition as defined in claim 28 which comprises N-{1-[2-(4-methoxyphenyl)ethyl]piperidin-4-yl}-N-(1H-pyrrol-1-yl)propanamide or a pharmaceutically acceptable salt thereof.

44. The composition as defined in claim 28 which comprises N-{1-[2-(4-methoxyphenyl)ethyl]piperidin-4-yl}-N-(1H-pyrrol-1-yl)cyanamide or a pharmaceutically acceptable salt thereof.

45. The composition as defined in claim 28 which comprises 1-(2-phenethyl)-4-[N-(n-propyl)-N-(1H-pyrrol-1-yl)]aminopiperidine or a pharmaceutically acceptable salt thereof.

46. The composition as defined in claim 28 which comprises N-[1-(2-phenylpropyl)piperidin-4-yl]-N-(1H-pyrrol-1-yl) propanamide or a pharmaceutically acceptable salt thereof.

47. The composition as defined in claim 28 which comprises N-[1-(2-phenylpropyl)piperidin-4-yl]-N-(1H-pyrrol-1-yl) carbamic acid ethyl ester or a pharmaceutically acceptable salt thereof.

48. The composition as defined in claim 28 which comprises N-[1-(2-phenethyl)piperidin-4-yl]-N-(1H-pyrrol-1-yl) carbamic acid-(n-butyl)ester or a pharmaceutically acceptable salt thereof.

49. The composition as defined in claim 28 which comprises N-[1-(2-phenethyl)piperidin-4-yl]-N-(1H-pyrrol-1-yl) acrylamide or a pharmaceutically acceptable salt thereof.

50. The composition as defined in claim 28 which comprises N-[1-(2-phenethyl)piperidin-4-yl]-N-(1H-pyrrol-1-yl)-N'-methylurea or a pharmaceutically acceptable salt thereof.

51. The composition as defined in claim 28 which comprises N-{1-[2-(2-thienyl)ethyl]piperidin-4-yl}-N-(1H-pyrrol-1-yl)propanamide or a pharmaceutically acceptable salt thereof.

52. The composition as defined in claim 28 which comprises N-[1-(2-phenethyl)piperidin-4-yl]-N-(1H-pyrrol-1-yl) cyclobutanecarboxylic acid amide or a pharmaceutically acceptable salt thereof.

53. The composition as defined in claim 28 which comprises N-{1-[2-(2-thienyl)ethyl]piperidin-4-yl}-N-(1H-pyrrol-1-yl)carbamic acid ethyl ester or a pharmaceutically acceptable salt thereof.

54. The composition as defined in claim 28 which comprises N-[1-(2-phenethyl)piperidin-4-yl]-N-(1H-pyrrol-1-yl) propanethioamide or a pharmaceutically acceptable salt thereof.

55. A method of alleviating pain in a mammal which comprises administering to a mammal in need thereof an effective pain relieving amount of a compound having the formula

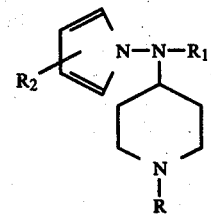

where R is hydrogen, loweralkyl, Arloweralkyl of the formula

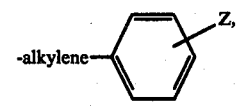

where Z is hydrogen, loweralkyl, loweralkoxy, halogen, CF$_3$, NO$_2$, NH$_2$; cycloalkylloweralkyl, loweralkenyl and thienylloweralkyl; R$_1$ is hydrogen, loweralkyl, loweralkylcarbonyl, loweralkoxycarbonyl, loweralkylthiocarbonyl, cyano, loweralkylaminocarbonyl, diloweralkylaminocarbonyl, cycloalkylcarbonyl, cycloalkylloweralkylcarbonyl and loweralkenylcarbonyl; R$_2$ is hydrogen, halogen and —CH$_3$; and the pharmaceutically acceptable addition salts thereof.

56. The method as defined in claim 55 wherein R is

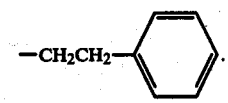

57. The method as defined in claim 56 wherein R$_1$ is loweralkoxycarbonyl, loweralkylcarbonyl and cyano.

58. The method as defined in claim 57 wherein R$_2$ is hydrogen.

59. The method as defined in claim 55 wherein said compound is N-(1-methylpiperidin-4-yl)-N-(1H-pyrrol-1-yl)propanamide or a pharmaceutically acceptable salt thereof.

60. The method as defined in claim 55 wherein said compound is N-[1-(2-phenethyl)piperidin-4-yl]-N-(1H-pyrrol-1-yl)propanamide or a pharmaceutically acceptable salt thereof.

61. The method as defined in claim 55 wherein said compound is N-[1-(2-phenylethyl)piperidin-4-yl]-N-(1H-pyrrol-1-yl)acetamide or a pharmaceutically acceptable salt thereof.

62. The method as defined in claim 55 wherein said compound is N-[1-(2-phenylethyl)piperidin-4-yl]-N-(1H-pyrrol-1-yl) carbamic acid ethyl ester or a pharmaceutically acceptable salt thereof.

63. The method as defined in claim 55 wherein said compound is N-[1-(2-phenylethyl)piperidin-4-yl]-N-(1H-pyrrol-1-yl) carbamic acid methyl ester or a pharmaceutically acceptable salt thereof.

64. The method as defined in claim 55 wherein said compound is N-[1-(2-phenethyl)piperidin-4-yl]-N-(1H-pyrrol-1-yl) cyanamide or a pharmaceutically acceptable salt thereof.

65. The method as defined in claim 55 wherein said compound is N-{1-[2-(4-chlorophenyl)ethyl]piperidin- 4-yl}-N-(1H-pyrrol-1-yl)carbamic acid ethyl ester or a pharmaceutically acceptable salt thereof.

66. The method as defined in claim 55 wherein said compound is N-{1-[2-(4-chlorophenyl)ethyl]piperidin-4-yl}-N-(1H-pyrrol-1-yl)propanamide or a pharmaceutically acceptable salt thereof.

67. The method as defined in claim 55 wherein said compound is N-[1-(n-butyl)piperidin-4-yl]-N-(1H-pyrrol-1-yl)carbamic acid ethyl ester or a pharmaceutically acceptable salt thereof.

68. The method as defined in claim 55 wherein said compound is N-[1-(n-butyl)piperidin-4-yl]-N-(1H-pyrrol-1-yl) propanamide or a pharmaceutically acceptable salt thereof.

69. The method as defined in claim 55 wherein said compound is 1-(2-phenethyl)-4-(1H-pyrrol-1-yl)aminopiperidine or a pharmaceutically acceptable salt thereof.

70. The method as defined in claim 55 wherein said compound is N-{1-[2-(4-methoxyphenyl)ethyl]piperidin-4-yl}-N-(1H-pyrrol-1-yl)propanamide or a pharmaceutically acceptable salt thereof.

71. The method as defined in claim 55 wherein said compound is N-{1-[2-(4-methoxyphenyl)ethyl]piperidin-4-yl}-N-(1H-pyrrol-1-yl)cyanamide or a pharmaceutically acceptable salt thereof.

72. The method as defined in claim 55 wherein said compound is 1-(2-phenethyl)-4-[N-(n-propyl)-N-(1H-pyrrol-1-yl)]aminopiperidine or a pharmaceutically acceptable salt thereof.

73. The method as defined in claim 55 wherein said compound is N-[1-(2-phenylpropyl)piperidin-4-yl]-N-(1H-pyrrol-1-yl) propanamide or a pharmaceutically acceptable salt thereof.

74. The method as defined in claim 55 wherein said compound is N-[1-(2-phenylpropyl)piperidin-4-yl]-N-(1H-pyrrol-1-yl) carbamic acid ethyl ester or a pharmaceutically acceptable salt thereof.

75. The method as defined in claim 55 wherein said compound is N-[1-(2-phenethyl)piperidin-4-yl]-N-(1H-pyrrol-1-yl) carbamic acid-(n-butyl)ester or a pharmaceutically acceptable salt thereof.

76. The method as defined in claim 55 wherein said compound is N-[1-(2-phenethyl)piperidin-4-yl]-N-(1H-pyrrol-1-yl) acrylamide or a pharmaceutically acceptable salt thereof.

77. The method as defined in claim 55 wherein said compound is N-[1-(2-phenethyl)piperidin-4-yl]-N-(1H-pyrrol-1-yl)-N'-methylurea or a pharmaceutically acceptable salt thereof.

78. The method as defined in claim 55 wherein said compound is N-{1-[2-(2-thienyl)ethyl]piperidin-4-yl}-N-(1H-pyrrol-1-yl)propanamide or a pharmaceutically acceptable salt thereof.

79. The method as defined in claim 55 wherein said compound is N-[1-(2-phenethyl)piperidin-4-yl]-N-(1H-pyrrol-1-yl) cyclobutanecarboxylic acid amide or a pharmaceutically acceptable salt thereof.

80. The method as defined in claim 55 wherein said compound is N-{1-[2-(2-thienyl)ethyl]piperidin-4-yl}-N-(1H-pyrrol-1-yl)carbamic acid ethyl ester or a pharmaceutically acceptable salt thereof.

81. The method as defined in claim 55 wherein said compound is N-[1-(2-phenethyl)piperidin-4-yl]-N-(1H-pyrrol-1-yl) propanethioamide or a pharmaceutically acceptable salt thereof.

82. A method of forming a compound having the formula

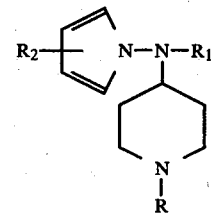

where R is hydrogen, loweralkyl, Arloweralkyl of the formula

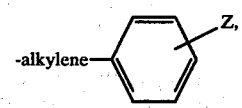

where Z is hydrogen, loweralkyl, loweralkoxy, halogen, $CF_3$, $NO_2$, $NH_2$, cycloalkylloweralkyl, loweralkenyl and thienylloweralkyl; $R_1$ is hydrogen, loweralkyl, loweralkylcarbonyl, loweralkoxycarbonyl, loweralkylthiocarbonyl, cyano, loweralkylaminocarbonyl, diloweralkylaminocarbonyl, cycloalkylcarbonyl, cycloalkylloweralkylcarbonyl and loweralkenylcarbonyl; $R_2$ is hydrogen, halogen and $-CH_3$; and the pharmaceutically acceptable addition salts thereof, which comprises: reacting a first compound of the formula

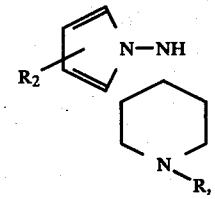

where R and $R_2$ are as previously defined with a second compound selected from

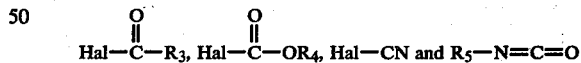

where Hal is a halogen, $R_3$ is $(C_1-C_5)$alkyl, a $(C_1-C_5)$alkenyl and cycloalkyl, $R_4$ is a $(C_1-C_6)$alkyl and $R_5$ is a $(C_1-C_6)$alkyl.

83. The method as defined in claim 82 wherein said second compound is

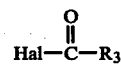

and which further comprises reducing the carbonyl of the resultant product to form a compound having the formula

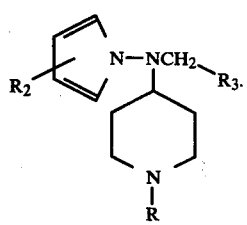

84. The method as defined in claim 82 wherein said second compound is

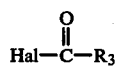

and which further comprises reacting the resultant reaction product with p-methoxyphenylthionophosphine sulfide dimer to form a compound having the formula

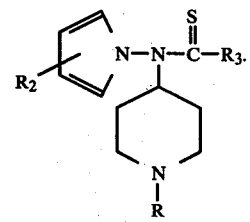

85. The method as defined in claim 82 wherein said second compound is $R_5-N=C=O$ and which further comprises alkylating the resultant reaction product to form a compound having the formula

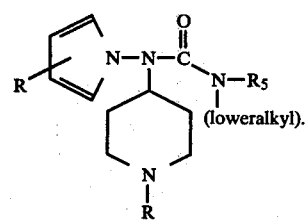

* * * * *